US009114397B2

(12) United States Patent
Cao

(10) Patent No.: US 9,114,397 B2
(45) Date of Patent: Aug. 25, 2015

(54) METHOD OF REDUCING CROSS-CONTAMINATION IN CONTINUOUS AMPLIFICATION REACTIONS IN A CHANNEL

(75) Inventor: Weidong Cao, Rockville, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 1084 days.

(21) Appl. No.: 12/257,036

(22) Filed: Oct. 23, 2008

(65) Prior Publication Data

US 2009/0111149 A1 Apr. 30, 2009

Related U.S. Application Data

(60) Provisional application No. 60/982,567, filed on Oct. 25, 2007.

(51) Int. Cl.

| | |
|---|---|
| ***C12Q 1/68*** | (2006.01) |
| ***B01L 3/00*** | (2006.01) |
| *B01L 7/00* | (2006.01) |
| *B01L 9/00* | (2006.01) |

(52) U.S. Cl.

CPC ............ *B01L 3/502784* (2013.01); *B01L 7/52* (2013.01); *B01L 9/52* (2013.01); *B01L 2300/0867* (2013.01)

(58) Field of Classification Search

None

See application file for complete search history.

(56) References Cited

U.S. PATENT DOCUMENTS 6,326,083 B1 12/2001 Yang et al.
6,383,755 B1 * 5/2002 Davis et al. ........................ 435/6
6,960,437 B2 11/2005 Enzelberger et al.
7,010,391 B2 3/2006 Handique et al.
2002/0119536 A1 * 8/2002 Stern ............................ 435/91.2
2005/0042639 A1 2/2005 Knapp et al.
2006/0078888 A1 4/2006 Griffiths et al.
2006/0257893 A1 11/2006 Takahashi et al.
2007/0111303 A1 5/2007 Inoue et al.
2007/0242105 A1 10/2007 Srinivasan et al.
2007/0243076 A1 10/2007 Kume et al.
2008/0003142 A1 1/2008 Link et al.
2008/0006535 A1 1/2008 Paik et al.
2008/0014589 A1 1/2008 Link et al.
2008/0023330 A1 1/2008 Viovy et al.
2008/0038810 A1 2/2008 Pollack et al.

(Continued)

FOREIGN PATENT DOCUMENTS

WO 2005/075683 A1 8/2005

OTHER PUBLICATIONS

New England Biolabs Taq DNA Polymerase with Thermopol Buffer [online] [retrieved on Dec. 29, 2010] retrieved from http://www.neb.com/nebecomm/products_Intl/productM0267.asp.*

(Continued)

*Primary Examiner* — Samuel Woolwine

(74) *Attorney, Agent, or Firm* — Rothwell, Figg, Ernst & Manbeck, P.C.

(57) ABSTRACT

The present invention relates to a method for reducing cross-contamination in continuous amplification reactions in channels of microfluidic devices. More specifically, the present invention relates to the use of specific materials continuously flowing in the channels to reduce adsorption of $MgCl_2$ and the concomitant adsorption of nucleic acid template to the channel surface, thereby reducing cross-contamination. This reduction of cross-contamination improves the efficiency and reproducibility of the amplification reaction, e.g., PCR.

28 Claims, 2 Drawing Sheets

(56) References Cited

U.S. PATENT DOCUMENTS

| | | | | |
|---|---|---|---|---|
| 2008/0085219 | A1 | 4/2008 | Beebe et al. | |
| 2009/0220966 | A1 * | 9/2009 | Stanley et al. | 435/6 |

OTHER PUBLICATIONS

Gentaur Taq Polymerase [online] [retrieved on Dec. 29, 2010] retrieved from http://www.bioxys.com/i_Gentaur/taq_polymerase.htm.*

Chiem et al. Microchip-based capillary electrophoresis for immunoassays: analysis of monoclonal antibodies and theophylline. Analytical Chemistry 69:373-378, 1997.*

Frackman et al. Betaine and DMSO: Enhancing Agents for PCR. Promega Notes No. 65, pp. 27-30, 1998.*

Zhang et al., "Survey and Summary, Miniaturized PCR chips for nucleic acid amplification and analysis: latest advances and future trends," Nucleic Acids Research, 35(13), pp. 4223-4237 (2007).

Henke et al., "Betaine improves the PCR amplification of GC-rich DNA sequences," Nucleic Acids Research, 25(19), pp. 3957-3958 (1997).

Lagally et al., "Single-Molecule DNA Amplification and Analysis in an Integrated Microfluidic Device," Analytical Chemistry, 73(3), pp. 565-570 (2001).

Kopp et al., "Chemical Amplification: Continuous-Flow PCR on a Chip," Science, 280, pp. 1046-1048 (1998).

Park et al., "Cylindrical compact thermal-cycling device for continuous-flow polymerase chain reaction," Analytical Chemistry, 75, pp. 6029-6033 (2003).

* cited by examiner

METHOD OF REDUCING CROSS-CONTAMINATION IN CONTINUOUS AMPLIFICATION REACTIONS IN A CHANNEL

CROSS-REFERENCE TO RELATED APPLICATION

This application claims the benefit of U.S. Provisional Patent Application Ser. No. 60/982,567, filed on Oct. 25, 2007, which is incorporated herein by reference in its entirety.

BACKGROUND

1. Field of the Invention

The present invention relates to methods for reducing cross-contamination in continuous amplification reactions in channels of microfluidic devices. This reduction of cross-contamination improves the efficiency and reproducibility of the amplification reaction, such as, for example, polymerase chain reaction (PCR).

2. Description of Related Art

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, correct identification of crime scene features, the ability to propagate industrial organisms and many other techniques. Determination of the integrity of a nucleic acid of interest can be relevant to the pathology of an infection or cancer. One of the most powerful and basic technologies to detect small quantities of nucleic acids is to replicate some or all of a nucleic acid sequence many times, and then analyze the amplification products. PCR is perhaps the most well-known of a number of different amplification techniques.

PCR is a powerful technique for amplifying short sections of DNA. With PCR, one can quickly produce millions of copies of DNA starting from a single template DNA molecule. PCR includes a three phase temperature cycle of denaturation of DNA into single strands, annealing of primers to the denatured strands, and extension of the primers by a thermostable DNA polymerase enzyme. This cycle is repeated so that there are enough copies to be detected and analyzed. In principle, each cycle of PCR could double the number of copies. In practice, the multiplication achieved after each cycle is always less than 2. Furthermore, as PCR cycling continues, the buildup of amplified DNA products eventually ceases as the concentrations of required reactants diminish. For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005) and *PCR Protocols A Guide to Methods and Applications*, M. A. Innis et al., eds., Academic Press Inc. San Diego, Calif. (1990).

Real-time PCR refers to a growing set of techniques in which one measures the buildup of amplified DNA products as the reaction progresses, typically once per PCR cycle. Monitoring the accumulation of products over time allows one to determine the efficiency of the reaction, as well as to estimate the initial concentration of DNA template molecules. For general details concerning real-time PCR see *Real-Time PCR: An Essential Guide*, K. Edwards et al., eds., Horizon Bioscience, Norwich, U.K. (2004).

More recently, a number of high throughput approaches to performing PCR and other amplification reactions have been developed, e.g., involving amplification reactions in microfluidic devices, as well as methods for detecting and analyzing amplified nucleic acids in or on the devices. Microfluidic systems are systems that have at least one channel through which a fluid may flow, which channel has at least one internal cross-sectional dimension, (e.g., depth, width, length, diameter) that is typically less than about 1000 micrometers. Thermal cycling of the sample for amplification is usually accomplished in one of two methods. In the first method, the sample solution is loaded into the device and the temperature is cycled in time, much like a conventional PCR instrument. In the second method, the sample solution is pumped continuously through spatially varying temperature zones. See, for example, Lagally et al. (*Analytical Chemistry* 73:565-570 (2001)), Kopp et al. (*Science* 280:1046-1048 (1998)), Park et al. (*Analytical Chemistry* 75:6029-6033 (2003)), Hahn et al. (WO 2005/075683), Enzelberger et al. (U.S. Pat. No. 6,960, 437) and Knapp et al. (U.S. Patent Application Publication No. 2005/0042639).

One challenge for continuous PCR in microchannels is cross-contamination of the nucleic acid samples. Several techniques have been developed in an attempt to avoid the DNA cross-contamination. For example, continuous-flow, high-throughput PCR amplification using droplets in an immiscible, fluorinated oil/fluorosurfactant solvent has been performed (Chabert et al., *Anal Chem* 78:7722-7728 (2006); Dorfman et al., *Anal Chem* 77:3700-3704 (2005)). The disadvantage of this technique is that it is a two phase system. In this system, the stability of the sample droplets in the oil phase is essential to obtain a successful amplification in the continuous-flow format. The addition of some additives, such as polyvinylpyrrolidone, has been suggested as an alternative for decreasing the cross-contamination (Kopp et al., Science 280(15): 1046-1048 (1998)). However, cross-contamination still remains an issue in this system. Thus, it is desired to develop additional techniques to reduce cross-contamination in continuous flow amplification reactions in microfluidic devices.

SUMMARY OF THE INVENTION

The present invention relates to methods for reducing cross-contamination in continuous amplification reactions in channels of microfluidic devices. The present invention also relates to substantially eliminating cross-contamination in such reactions. More specifically, the present invention relates to the use of specific materials continuously flowing in the channels to reduce adsorption of $MgCl_2$ and the concomitant adsorption of nucleic acid template to the channel surface, thereby reducing cross-contamination. This reduction of cross-contamination improves the efficiency and reproducibility of the amplification reaction, such as, for example, PCR.

According to one aspect, the present invention provides methods of performing continuous flow amplification reactions in a microfluidic channel with reduced cross-contamination. The present invention also provides methods of performing continuous flow amplification reactions in a microfluidic channel in which the cross-contamination is substantially eliminated. In one embodiment, the method comprises continuously and alternatively introducing a plug of a sample solution and a plug of a cleaning solution into a microfluidic channel in a continuous flow. In some embodiment, the sample solution comprises $MgCl_2$ and dNTPs, and the cleaning solution comprises one or more zwitterions. In additional embodiments, the zwitterion is a betaine. An example of a betaine useful in the present invention is trimethylglycine. In some embodiments, a solution containing primer and polymerase is introduced into each plug of the sample solution as each plug flows through a portion of the microfluidic channel. The methods further include performing amplification reactions on the plugs of sample solutions as they continuously flow through the microfluidic channel. In accordance with aspects of the invention, the cleaning solution reduces $MgCl_2$ adherence to the microfluidic channel surface to reduce cross-contamination of nucleic acids in the amplification reactions.

In other embodiments, the sample solution comprises $MgCl_2$, dNTPs, Tris buffer, a nucleic acid sample and one or more zwitterions. In other embodiments, the cleaning solution comprises Tris buffer, KCl and one or more zwitterions. In further embodiments, a primer solution is introduced into each plug of a sample solution and each plug of the cleaning solution as the plugs continuously flow through the microfluidic channel. In some embodiments, the primer solution comprises amplification primers, Tris buffer, KCl and one or more zwitterions. In some embodiments, the methods also include introducing a polymerase solution into each plug of a sample solution and each plug of the cleaning solution as the plugs continuously flow through the microfluidic channel. In some embodiments, the polymerase solution comprises polymerase, Tris buffer, and one or more zwitterions. The method further includes performing amplification reactions on the plugs of sample solutions as they continuously flow through the microfluidic channel. In accordance with aspects of the invention, the cleaning solution reduces $MgCl_2$ adherence to the microfluidic channel surface to reduce cross-contamination of nucleic acids in the amplification reactions because the nucleic acids in the sample solutions can no longer adhere to the $MgCl_2$ in the channels.

In other embodiments, multiple sample solutions are introduced into the microfluidic channel wherein each sample solution is introduced as a sample plug. In one embodiment, the multiple sample solutions are sample solutions comprising different nucleic acid samples. In another embodiment, a portion of the multiple sample solutions are different replicates of the same nucleic acid sample. In a further embodiment, the multiple sample solutions are sample solutions comprising different nucleic acid samples and a portion of the multiple sample solutions are different replicates of the same nucleic acid sample. In some embodiments, the primer solution is introduced into the plugs first, and the polymerase solution is introduced into the plugs second. In other embodiments, the polymerase solution is introduced into the plugs first, and the primer solution is introduced into the plugs second.

In some embodiments, the concentration of the one or more zwitterions is between about 0.05 M and about 2.0 M. In additional embodiments, the concentration of the one or more zwitterions is between about 0.5 M and about 1.5 M. In other embodiments, the concentration of the one or more zwitterions is about 1 M. In some embodiments, the Tris buffer concentration is between about 10 mM and about 30 mM. In additional embodiments, the Tris buffer concentration is between about 10 mM and about 20 mM. In other embodiments, the Tris buffer concentration is about 10 mM. In some embodiments, the KCl concentration is between about 40 mM and about 100 mM. In additional embodiments, the KCl concentration is between about 50 mM and 75 mM. In other embodiments, the KCl concentration is about 50 mM. In some embodiments, the primer concentration is between about 0.1 μM and about 1.0 μM. In additional embodiments, the primer concentration is between about 0.1 μM and 0.5 μM. In other embodiments, the primer concentration is about 0.2 μM. In some embodiments, the amount of polymerase is between about 0.01 units/μL and about 5.0 units/μL. In additional embodiments, the amount of polymerase is between about 0.1 units/μL and about 2.0 units/μL. In other embodiments, the amount of polymerase is about 0.3 units/μL. In some embodiments, the $MgCl_2$ concentration is between about 1 mM and about 8 mM. In additional embodiments, the $MgCl_2$ concentration is between about 1 mM and about 5 mM. In other embodiments, the $MgCl_2$ concentration is about 2 mM. In some embodiments, the concentration of each dNTP is between about 0.1 mM and about 4 mM. In additional embodiments, the concentration of each dNTP is between about 0.5 mM and about 2.0 mM. In other embodiments, the concentration of each dNTP is about 1.0 mM.

BRIEF DESCRIPTION OF THE FIGURES

The accompanying figures, which are incorporated herein and form part of the specification, illustrate various embodiments of the present invention.

DETAILED DESCRIPTION OF THE PREFERRED EMBODIMENTS

Figure 1:
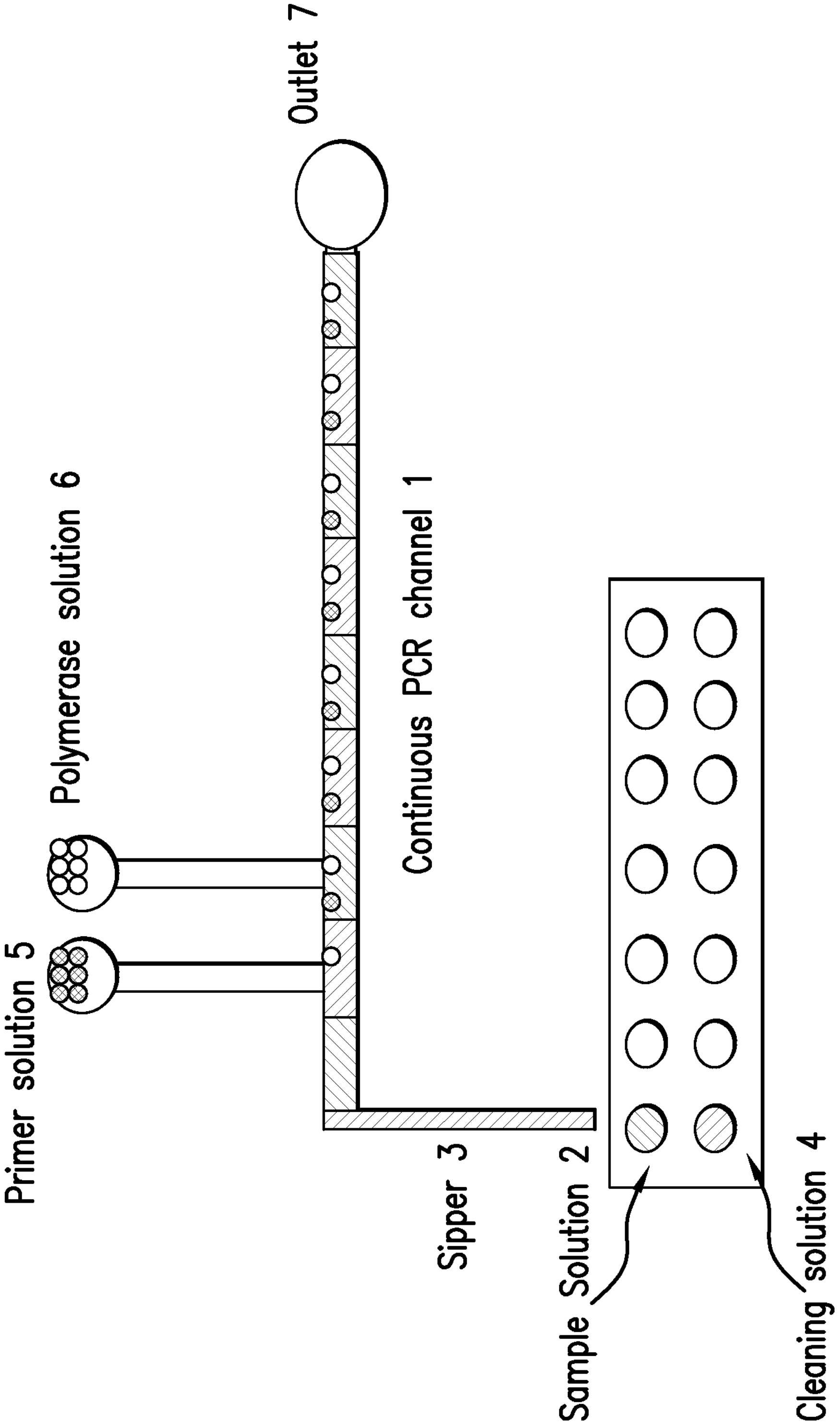
FIG. 1 is a schematic illustrating a method and system for performing the method in accordance with one embodiment of the present invention.

The present invention has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, N.Y., Gait, *Oligonucleotide Synthesis: A Practical Approach,* 1984, IRL Press, London, Nelson and Cox (2000), Lehninger, *Principles of Biochemistry* 3rd Ed., W. H. Freeman Pub., New York, N.Y. and Berg et al. (2002) *Biochemistry,* 5th Ed., W. H. Freeman Pub., New York, N.Y., all of which are herein incorporated in their entirety by reference for all purposes.

The present invention relates to a method for reducing cross-contamination in continuous amplification reactions in channels of microfluidic devices. The present invention also relates to substantially eliminating cross-contamination in such reactions. More specifically, the present invention relates to the use of specific materials continuously flowing in the channels to reduce adsorption of $MgCl_2$ and the concomitant adsorption of nucleic acid template to the channel surface, thereby reducing cross-contamination. This reduction of cross-contamination improves the efficiency and reproducibility of the amplification reaction, such as, for example, PCR.

The present invention provides a system and method for reducing cross-contamination in continuous amplification reactions in channels of microfluidic devices, i.e. in microchannels. The present invention also provides a method of performing continuous flow amplification reactions in a microfluidic channel in which the cross-contamination is substantially eliminated. Microfluidic refers to a system or device having fluidic conduits or chambers that are generally fabricated at the micron to submicron scale, e.g., typically having at least one cross-sectional dimension in the range of from about 0.1 μm to about 500 μm. A microchannel is a channel having at least one microscale dimension. The microfluidic systems are generally fabricated from materials that are compatible with components of the fluids present in the particular experiment of interest. Customarily, such fluids are substantially aqueous in composition, but may comprise other agents or solvents such as alcohols, acetones, ethers, acids, alkanes, or esters. Suitable materials used in the manufacture of microfuidic devices are described, for example, in U.S. Pat. No. 6,326,083 and U.S. Patent Application Publication No. 2007/0246076 A1 and include silica based substrates such as glass and polymeric materials, e.g., plastics, such as polymethylmethacrylate (PMMA), polycarbonate, polytetrafluoroethylene (TEFLON), polyvinylchloride (PVC), polydimethylsiloxane (PDMS), polysulfone, polystyrene, polymethylpentene, polypropylene, polyethylene, polyvinylidine fluoride, ABS (acrylonitrile-butadiene-styrene copolymer), epoxy type polymers (such as SU-8, a negative, epoxy-type, near-UV photoresist), and the like. Such polymeric substrates are readily manufactured using available microfabrication techniques or from microfabricated masters, using well known molding techniques.

In one embodiment, the method comprises continuously and alternatively introducing a plug of a sample solution and a plug of a cleaning solution into a microfluidic channel in a continuous flow, introducing a primer solution into each plug of a sample solution and each plug of the cleaning solution as the plugs continuously flow through the microfluidic channel, introducing a polymerase solution into each plug of a sample solution and each plug of the cleaning solution as the plugs continuously flow through the microfluidic channel, and performing amplification reactions on the plugs of sample solutions as they continuously flow through the microfluidic channel. In some non-limiting embodiments, the sample solution comprises $MgCl_2$, dNTPs, Tris buffer, a nucleic acid sample and one or more zwitterions. In additional embodiments, the zwitterion is a betaine. As used herein, the term "betaine" refers to any neutral chemical molecule having charge separated forms with an onium group which bears no hydrogen atoms and that is not adjacent to an anionic atom or group. Examples of onium groups include, but are not limited to, an ammonium group and a phosphonium group. An example of an anionic group is a carboxylic acid group. A non-limiting example of a betaine useful in the present invention is trimethylglycine.

In other non-limiting embodiments, the cleaning solution comprises Tris buffer, KCl and one or more zwitterions. In additional non-limiting embodiments, the primer solution comprises amplification primers, Tris buffer, KCl and one or more zwitterions. In further non-limiting embodiments, the polymerase solution comprises polymerase, Tris buffer and one or more zwitterions. The primer solution and the polymerase solution can be added to the plugs in any order. For example, the primer solution can be added first, and the polymerase solution can be added second. Alternatively, the polymerase solution can be added first, and the primer solution can be added second.

In one embodiment, the cleaning solution reduces $MgCl_2$ adherence to the mircrofluidic channel surface to reduce cross-contamination of nucleic acids in the amplification reactions because the nucleic acids in the sample solutions can no longer adhere to the $MgCl_2$ in the channels. In some embodiments, multiple sample solutions are introduced into the microfluidic channel wherein each sample solution is introduced as a sample plug. In one embodiment, the multiple sample solutions are sample solutions comprising different nucleic acid samples. In another embodiment, a portion of the multiple sample solutions comprise different replicates of the same nucleic acid sample. In a further embodiment, the multiple sample solutions are sample solutions comprising different nucleic acid samples and a portion of the multiple sample solutions comprise different replicates of the same nucleic acid sample.

The nucleic acid samples may contain the same template or different templates. If the same template is present in all of the nucleic acid samples, the same primer solution can be used for each. If different templates are present in the various nucleic acid samples, different primer solutions, each containing the appropriate primers for the particular template, are used. The nucleic acid samples are prepared using conventional techniques and kits that are well known to the skilled artisan and that are commercially available.

In other embodiments, the method comprises continuously and alternatively introducing a plug of a sample solution and a plug of a cleaning solution into a microfluidic channel in a continuous flow in which the sample solution comprises $MgCl_2$ and dNTPs, and the cleaning solution comprises one or more zwitterions. A solution containing primer and polymerase is introduced into each plug of the sample solution as each plug flows through a portion of the microfluidic channel. The method further includes performing amplification reactions on the plugs of sample solutions as they continuously flow through the microfluidic channel. In accordance with aspects of the invention, the cleaning solution reduces $MgCl_2$ adherence to the microfluidic channel surface to reduce cross-contamination of nucleic acids in the amplification reactions.

In some embodiments, the concentration of the one or more zwitterions is between about 0.05 M and about 2.0 M. In additional embodiments, the concentration of the one or more zwitterions is between about 0.5 M and about 1.5 M. In other embodiments, the concentration of the one or more zwitterions is about 1 M. In some embodiments, the Tris buffer concentration is between about 10 mM and about 30 mM. In additional embodiments, the Tris buffer concentration is between about 10 mM and about 20 mM. In other embodiments, the Tris buffer concentration is about 10 mM. In some embodiments, the KCl concentration is between about 40 mM and about 100 mM. In additional embodiments, the KCl concentration is between about 50 mM and 75 mM. In other embodiments, the KCl concentration is about 50 mM. In some embodiments, the primer concentration is between about 0.1 μM and about 1.0 μM. In additional embodiments, the primer concentration is between about 0.1 μM and 0.5 μM. In other embodiments, the primer concentration is about 0.2 μM. In some embodiments, the amount of polymerase is between about 0.01 units/μL and about 5.0 units/μL. In additional embodiments, the amount of polymerase is between about 0.1 units/μL and about 2.0 units/μL. In other embodiments, the amount of polymerase is about 0.3 units/μL. In some embodiments, the $MgCl_2$ concentration is between about 1 mM and about 8 mM. In additional embodiments, the $MgCl_2$ concentration is between about 1 mM and about 5 mM. In other embodiments, the $MgCl_2$ concentration is about 2 mM. In some embodiments, the concentration of each dNTP is between about 0.1 mM and about 4 mM. In additional embodiments, the concentration of each dNTP is between about 0.5 mM and about 2.0 mM. In other embodiments, the concentration of each dNTP is about 1.0 mM.

In some embodiments, the sample solution further comprises dyes or other compounds that are capable of detecting amplified products. Such dyes and compounds are well known in the art. Several different real-time detection chemistries now exist to indicate the presence of amplified DNA. Most of these depend upon fluorescence indicators that change properties as a result of the PCR process. Among these detection chemistries are DNA binding dyes (such as SYBR® Green) that increase fluorescence efficiency upon binding to double stranded DNA. Other real-time detection chemistries utilize Foerster resonance energy transfer (FRET), a phenomenon by which the fluorescence efficiency of a dye is strongly dependent on its proximity to another light absorbing moiety or quencher. These dyes and quenchers are typically attached to a DNA sequence-specific probe or primer. Among the FRET-based detection chemistries are hydrolysis probes and conformation probes. Hydrolysis probes (such as the TaqMan probe) use the polymerase enzyme to cleave a reporter dye molecule from a quencher dye molecule attached to an oligonucleotide probe. Conformation probes (such as molecular beacons) utilize a dye attached to an oligonucleotide, whose fluorescence emission changes upon the conformational change of the oligonucleotide hybridizing to the target DNA.

The methods, and system for performing the methods, in accordance with one aspect of the present invention are illustrated in connection with FIG. 1. FIG. 1 illustrates a continuous PCR channel 1 in which PCR reactions are performed using conventional microfluidic techniques. A plug of a sample solution 2 as described herein is introduced into the microchannel using sipper 3. A plug of the cleaning solution 4 as described herein is then introduced into the microchannel using sipper 3. In the continuous flow format of the present invention, a plug of a sample solution 2 is alternated with a plug of the cleaning solution 4 and they are continuously introduced into the microchannel. In some embodiments, as each sample and cleaning plug proceeds through the microchannel, a primer solution 5 as described herein is introduced into each sample and cleaning plug and then a polymerase solution 6 as described herein is introduced into each sample and cleaning plug. After the PCR reactions in each sample solution 2 are completed during continuous flow through the continuous PCR channel, the amplified products and the cleaning solution 4 flow through outlet 7.

In other embodiments, as each sample plug proceeds through the microchannel, a primer solution 5 as described herein is introduced into each sample plugs only and then a polymerase solution 6 as described herein is introduced into each sample plugs only. After the PCR reactions in each sample solution 2 are completed during continuous flow through the continuous PCR channel, the amplified products and the cleaning solution 4 flow through outlet 7. In still other embodiments, the primer solution and the polymerase solution are contained in a single solution and added to the sample plugs alone or both the sample plugs and the cleaning plugs.

Figure 2:
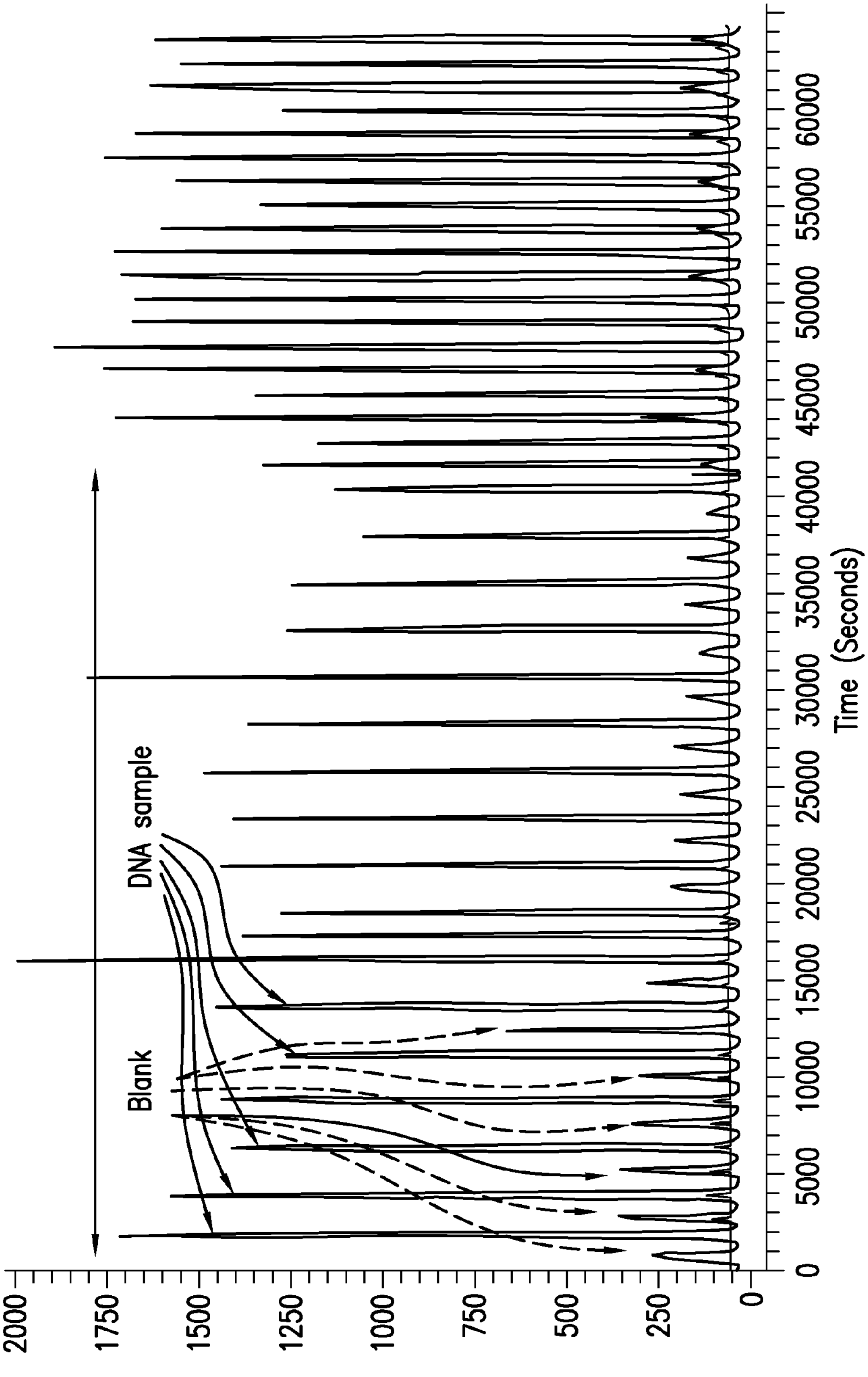
FIG. 2 shows the results of an experiment in accordance with the present invention in which PCR amplification reactions were conducted in the microchannels of a microfluidic device without cross-contamination of the nucleic acids.

An experiment was conducted to demonstrate the reduction of cross-contamination in continuous flow PCR reactions in a microchannel using the method and system in accordance with one aspect of the present invention. The parameters of this experiment are shown in Table 1. The human DNA was the sample DNA and the salmonella DNA was the non-template control. Each DNA was sonicated for five minutes before use. The solutions were continuously flowed through the microchannels in the following order: sample DNA solution, cleaning solution, non-template control solution, cleaning solution, etc. The cleaning solution comprised 10 mM Tris buffer, 50 mM KCl and 1 M betaine (trimethylglycine). The thermal cycling conditions were: denature at 91° C. for 10 seconds; anneal at 60° C. for 15 seconds; and extension at 70° C. for 10 seconds. Fifty cycles of PCR were conducted in the microfluidic device. The results are shown in FIG. 2.

TABLE 1

PCR Parameters

Sample DNA Solution

| | | | | |
|---|---|---|---|---|
| | % Contribution | | | 57.7 |
| | Total Volume | | | 35.0 μL |
| | Master Mix (μL) 5 | Volume (μL) | Channel Concentration | Stock Concentration |
| Human Template | 10.0 | 2.0 | 0.46 cp/nL | 46 ng/μL |
| Tris Buffer | 17.5 | 3.5 | 1 X | 10 X |
| Betaine | 35.0 | 7.0 | 1 M | 5 M |
| Tween 20 | 7.0 | 1.4 | 0.04% | 1% |
| DMSO | 3.5 | 0.7 | 2% | 100% |
| Alexa Fluor | 1.7 | 0.3 | 57 nM | 10000 nM |
| LCGreen Plus | 30.3 | 6.1 | 1 X | 10 X |
| dNTPs | 6.1 | 0.6 | 0.2 mM | 10 mM |
| $Mg^{2+}$ | 7.0 | 1.4 | 2 mM | 50 mM |
| $H_2O$ | 59.9 | 12.0 | | |
| Total Volume | 175.0 | 35.0 | | |

Non-Template Control Solution

| | | | | |
|---|---|---|---|---|
| | % Contribution | | | 57.7 |
| | Total Volume | | | 35.0 μL |
| | Master Mix (μL) 5 | Volume (μL) | Channel Concentration | Stock Concentration |
| *Salmonella* DNA | | | 50 cp/nL | 60 ng/μL |
| Tris Buffer | 17.5 | 3.5 | 1 X | 10 X |
| Betaine | 35.0 | 7.0 | 1 M | 5 M |
| Tween 20 | 7.0 | 1.4 | 0.04% | 1% |
| DMSO | 3.5 | 0.7 | 2% | 100% |
| Alexa Fluor | 1.7 | 0.3 | 57 nM | 10000 nM |
| LCGreen Plus | 30.3 | 6.1 | 1 X | 10 X |
| dNTPs | 6.1 | 0.6 | 0.2 mM | 10 mM |
| $Mg^{2+}$ | 7.0 | 1.4 | 2 mM | 50 mM |
| $H_2O$ | 59.9 | 12.0 | | |
| Total Volume | 175.0 | 35.0 | | |

Primer Solution

| | | | | |
|---|---|---|---|---|
| | % Contribution | | 28.6 | |
| | Total Volume | | 15.0 | |
| | Master Mix (μL) 20 | Volume (μL) | Channel Concentration | Stock Concentration |
| Forward Primer | 10.5 | 0.5 | 1 μM | 100 μM |
| Reverse Primer | 10.5 | 0.5 | 1 μM | 100 μM |
| Tris Buffer | 30.0 | 1.5 | 1 X | 10 X |
| Betaine | 60.0 | 3.0 | 1 M | 5 M |
| Tween 20 | 12.0 | 0.6 | 0.04% | 1% |
| DMSO | 6.0 | 0.3 | 2% | 100% |

TABLE 1-continued

| PCR Parameters | | | | |
|---|---|---|---|---|
| Alexa Fluor | 2.7 | 0.1 | 26 nM | 26 nM |
| $H_2O$ | 168.3 | 8.4 | | |
| Total Volume | 300 | 15 | | |

| Polymerase Solution | |
|---|---|
| % Contribution | 13.7 |
| Total Volume | 30.0 |

| | Master Mix (μL) 10 | Volume (μL) | Channel Concentration | Stock Concentration |
|---|---|---|---|---|
| Taq Polymerase | 87.6 | 8.8 | 0.2 U/μL | 5.0 U/μL |
| Tris Buffer | 30.0 | 3.0 | 1 X | 10 X |
| Betaine | 60.0 | 6.0 | 1 M | 5 M |
| Tween 20 | 12.0 | 1.2 | 0.04% | 1% |
| Glycerol | 54.7 | 5.5 | 3.25% | 50% |
| $H_2O$ | 55.7 | 5.6 | | |
| Total Volume | 300.0 | 30.0 | | |

Notes:
$Mg^{2+}$ was present as $MgCl_2$.
Betaine as used was trimethylglycine.

FIG. 2 shows the total fluorescence from 8 microchannels in the microfluidic device over the period of the experiment, i.e., more than 60,000 seconds, for the sample plugs (DNA sample) and the cleaning solution (Blank). For approximately 11.1 hours and 34 PCR reactions, the cleaning solution only showed background levels of fluorescence. This result indicates that any $MgCl_2$ that may be adsorbing to the surface of the microchannels from the sample plugs and any concomitant nucleic acids that then stick to the $MgCl_2$ are being removed by the cleaning solution, thus reducing cross-contamination between the DNA samples for this time period. This experiment reflects that continuous PCR reactions were performed for approximately 11.1 hours in the microchannels without contamination using the method in accordance with one embodiment of the present invention.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of performing continuous flow amplification reactions in a microfluidic channel with reduced cross-contamination, the method comprising:

(a) introducing a plug of a sample solution into a microfluidic channel, then introducing a plug of a cleaning solution into the microfluidic channel, whereby the plugs are introduced in a continuous flow such that the plugs of sample solution alternate with the plugs of cleaning solution in the microfluidic channel, wherein the sample solution comprises $MgCl_2$ and dNTPs, and wherein the cleaning solution comprises one or more zwitterions, wherein the plug of the sample solution and the plug of the cleaning solution are sequentially introduced into the microfluidic channel through the same inlet port;

(b) introducing a solution comprising a primer and a solution comprising a polymerase into each plug of the sample solution as each plug flows through a portion of the micro fluidic channel; and (c) performing amplification reactions on the plugs of sample solutions as they continuously flow through the microfluidic channel, wherein the cleaning solution reduces $MgCl_2$ adherence to the microfluidic channel surface; and wherein cross-contamination of nucleic acids in the amplification reactions is substantially eliminated.

2. The method of claim 1, wherein multiple sample solutions are introduced into the microfluidic channel and wherein each sample solution is introduced as a sample plug.

3. The method of claim 2, wherein the multiple sample solutions are sample solutions comprising different nucleic acid samples.

4. The method of claim 2, wherein a portion of the multiple sample solutions are different replicates of the same nucleic acid sample.

5. The method of claim 1, wherein the concentration of the one or more zwitterions is between about 0.05 M and about 2.0 M.

6. The method of claim 5, wherein the concentration of the one or more zwitterions is between about 0.5 M and about 1.5 M.

7. The method of claim 5, wherein the concentration of the one or more zwitterions is about 1M.

8. The method of claim 1, wherein the sample solution comprises $MgCl_2$, dNTPs, Tris buffer, a nucleic acid sample and one or more zwitterions, and wherein the cleaning solution comprises Tris buffer, KCl and one or more zwitterions.

9. The method of claim 1, wherein the primer solution comprises amplification primers, Tris buffer, KCl and one or more zwitterions.

10. The method of claim 1, wherein the polymerase solution comprises polymerase, Tris buffer and one or more zwitterions.

11. The method of claim 1, wherein the primer concentration is between about 0.1 mM and about 1.0 mM.

12. The method of claim 11, wherein the primer concentration is between about 0.1 mM and about 0.5 mM.

13. The method of claim 12, wherein the primer concentration is about 0.2 mM.

14. The method of claim 1, wherein the amount of polymerase is equivalent to between 0.01 units/mL and 5.0 units/mL of Taq polymerase.

15. The method of claim 14, wherein the amount of polymerase is equivalent to between 0.1 units/mL and 2.0 units/mL of Taq polymerase.

16. The method of claim 15, wherein the amount of polymerase is equivalent to 0.3 units/mL of Taq polymerase.

17. The method of claim 1, wherein the $MgCl_2$ concentration is between about 1 mM and about 8 mM.

18. The method of claim 17, wherein the $MgCl_2$ concentration is between about 1 mM and about 5 mM.

19. The method of claim 18, wherein the $MgCl_2$ concentration is about 2 mM.

20. The method of claim 1, wherein the primer solution is introduced into each plug of a sample solution and each plug of the cleaning solution as the plugs continuously flow through the microfluidic channel, and wherein the polymerase solution is introduced into each plug of a sample solution and each plug of the cleaning solution as the plugs continuously flow through the microfluidic channel.

21. The method of claim 1, wherein the primer solution is introduced into the plugs first and the polymerase solution is introduced into the plugs second.

22. The method of claim 1, wherein the polymerase solution is introduced into the plugs first and the primer solution is introduced into the plugs second.

23. The method of claim 1, wherein said one or more zwitterions comprises a betaine.

24. The method of claim 23, wherein said betaine is trimethylglycine.

25. A method of performing continuous flow amplification reactions in a microfluidic channel with reduced cross-contamination, the method comprising:

(a) introducing a plug of a sample solution into a microfluidic channel, then introducing a plug of a cleaning solution into the microfluidic channel, whereby the plugs are introduced in a continuous flow such that the plugs of sample solution alternate with the plugs of cleaning solution in the microfluidic channel, wherein the sample solution comprises $MgCl_2$, dNTPs, Tris buffer, a nucleic acid sample and one or more zwitterions, and wherein the cleaning solution comprises Tris buffer, KCl and one or more zwitterions, wherein the plug of the sample solution and the plug of the cleaning solution are sequentially introduced into the microfluidic channel through the same inlet port;

(b) introducing a primer solution into each plug of a sample solution and each plug of the cleaning solution as the plugs continuously flow through the microfluidic channel, wherein the primer solution comprises amplification primers, Tris buffer, KCl and one or more zwitterions;

(c) introducing a polymerase solution into each plug of a sample solution and each plug of the cleaning solution as the plugs continuously flow through the micro fluidic channel, wherein the polymerase solution comprises polymerase, Tris buffer and one or more zwitterions; and (d) performing amplification reactions on the plugs of sample solutions as they continuously flow through the microfluidic channel, wherein the cleaning solution reduces $MgCl_2$ adherence to the microfluidic channel surface; and wherein cross-contamination of nucleic acids in the amplification reactions is substantially eliminated.

26. The method of claim 25, wherein the concentration of the one or more zwitterions is between about 0.05 M and about 2.0 M, the Tris buffer concentration is between about 10 mM and about 30 mM, the KCl concentration is between about 40 mM and about 100 mM, the primer concentration is between about 0.1 mM and about 1.0 mM, the amount of polymerase is equivalent to between 0.01 units/mL and 5.0 units/mL of Taq polymerase, the $MgCl_2$ concentration is between about 1 mM and about 8 mM and the concentration of each dNTP is between about 0.1 mM and about 4 mM.

27. The method of claim 26, wherein the concentration of the one or more zwitterions is between about 0.05 M and about 1.5 M, the Tris buffer concentration is between about 10 mM and about 20 mM, the KCl concentration is between about 50 mM and about 75 mM, the primer concentration is between about 0.1 mM and about 0.5 mM, the amount of polymerase is equivalent to between 0.1 units/mL and 2.0 units/mL of Taq polymerase, the $MgCl_2$ concentration is between about 1 mM and about 5 mM and the concentration of each dNTP is between about 0.5 mM and about 2 mM.

28. The method of claim 26, wherein the concentration of the one or more zwitterions is about 1 M, the Tris buffer concentration is about 10 mM, the KCl concentration is about 50 mM, the primer concentration is about 0.2 mM, the amount of polymerase is equivalent to 0.3 units/mL of Taq polymerase, the $MgCl_2$ concentration is about 2 mM and the concentration of each dNTP is about 1 mM.

* * * * *